US008765448B2

(12) United States Patent
Rolland et al.

(10) Patent No.: US 8,765,448 B2
(45) Date of Patent: Jul. 1, 2014

(54) METHODS AND MEANS FOR EXACT REPLACEMENT OF TARGET DNA IN EUKARYOTIC ORGANISMS

(75) Inventors: Anne Rolland, Fontaine sur Saone (FR); Manuel Dubald, Raleigh, NC (US); Michiel Van Lookeren Campagne, Chapel Hill, NC (US); Rene Ruiter, Heusden (BE)

(73) Assignee: Bayer Cropscience, N.V., Diegem (BE)

( * ) Notice: Subject to any disclaimer, the term of this patent is extended or adjusted under 35 U.S.C. 154(b) by 756 days.

(21) Appl. No.: 12/663,172

(22) PCT Filed: Jun. 3, 2008

(86) PCT No.: PCT/EP2008/004524
§ 371 (c)(1),
(2), (4) Date: Dec. 4, 2009

(87) PCT Pub. No.: WO2008/148559
PCT Pub. Date: Dec. 11, 2008

(65) Prior Publication Data
US 2010/0175143 A1    Jul. 8, 2010

Related U.S. Application Data

(60) Provisional application No. 60/933,814, filed on Jun. 8, 2007.

(30) Foreign Application Priority Data

Jun. 5, 2007  (EP) ..................................... 07010998

(51) Int. Cl.
*C12N 1/00* (2006.01)
*C12N 15/87* (2006.01)
*C12N 15/74* (2006.01)

(52) U.S. Cl.
USPC .................. 435/254.11; 435/463; 435/257.2; 435/477; 435/478; 800/278

(58) Field of Classification Search
None
See application file for complete search history.

(56) References Cited

U.S. PATENT DOCUMENTS

2005/0172365 A1*  8/2005  Puchta et al. ................. 800/294

FOREIGN PATENT DOCUMENTS

| WO | WO 94/18313 A1 | 8/1994 |
| WO | WO 95/09233 A1 | 4/1995 |
| WO | WO 96/14408 A2 | 5/1996 |
| WO | WO 97/30166 A1 | 8/1997 |
| WO | WO 00/46386 A2 | 8/2000 |
| WO | WO 03/004659 A2 | 1/2003 |
| WO | WO 03/080809 A2 | 10/2003 |
| WO | WO 2004/067736 A2 | 8/2004 |
| WO | WO 2004/067753 A2 | 8/2004 |
| WO | WO 2005/049842 * | 6/2005 |
| WO | WO 2006/105946 * | 10/2006 |
| WO | WO 2006/105946 A2 | 10/2006 |
| WO | WO 2007/047859 A2 | 4/2007 |
| WO | WO 2007/049095 A1 | 5/2007 |
| WO | WO 2007/049156 A2 | 5/2007 |
| WO | WO 2007/93836 A1 | 8/2007 |
| WO | WO 2008/37436 A1 | 4/2008 |

OTHER PUBLICATIONS

Orel et al, Different pathways of homologous recombination are used for the repair of double-strand breaks within tandemly arranged sequences in the plant genome, 2003 Plant Journal 35:604-612.*
Sugawara et al. 1992, Molecular and Cellular Biology 12:563-575.*
Chilton, et al., Targeted integration of T-DNA into the tobacco genome at double-stranded breaks: New insights on the mechanism of T-DNA integration, Plant Physio., Nov. 1, 2003, 133(3):956-965.
Colleaux, et al., PNAS, 1988, 85:6022-6026.
Cordts, et al., Plant J., 2001, 25(1):103-144.
Drouaud, et al., Sex Plant Reprod., 2000, 13:29-35.
Engel, et al., The Plant J., 2003, 34:697-707.
Fourgoux-Nicol, et al., Plant Mol. Bio., 1999, 40:857-872.
Galli, et al, Genetics, 2003, 165(4):2093-2105.
Haerizadeh, et al., Sci., 2006, 313:496-499.
Isalan, et al., Nat. Biotech., 2001, 19:656-660.
Kalderon, et al., Cell, 1984, 39:499-509.
Liu, et al., PNAS, 1997, 94:5525-5530.
Marton, et al., Sci., 2005, 307:573-576.
Okada, et al., Plant and Cell Physio., 2005, 46:797-802.
Pacher, et al., Two unlinked double-strand breaks can induce reciprocal exchanges in plant genomes via homologous recombination and nonhomologous end joining, Genetics, 2007, 175(1):21-29.
Puchta, et al., PNAS, 1996, 93:5055-5060.
Raikhel, Plant Physio., 1992, 100:1627-1632.
Rotman, et al., Curr. Bio., 2005, 15(3):244-248.
Singh, et al., FEBS Lett., 2003, 542(1-3):47-52.
Tzfira, et al., Plant Physio., 2003, 133:1011-1023.
Wright, et al., High-frequency homologous recombination in plants mediated by zinc-finger nucleases, Plant J., 2005, 44(4):693-705.
Xu, et al., Plant J., 1998, 13(6):823-829.
Xu, et al., PNAS, 1999, 96(5):2554-2558.
Xu, et al., Plant Mol. Bio., 1999, 39:607-614.
Yang, et al., Plant Physio., 2005, 139(3):1421-1432.
Yu, et al., Plant Physio., 2005, 139(4):1853-1869.
GenBank Accession No. BE225314 "RSCDS0127 Rice sperm cells lambda TriplEx2 cDNA library *Oryza sativa* Indica Group cDNA similar to polyubiquitin, mRNA sequence." (2000).
GenBank Accession No. BE225323 "RSCDS0136 Rice sperm cells lambda TriplEx2 cDNA library *Oryza sativa* Indica Group cDNA, mRNA sequence." (2000).
GenBank Accession No. BF475189 "ESTsub1A2(1) Subtracted rice sperm cells cDNA Library *Oryza sativa* Indica Group cDNA, mRNA sequence." (2000).
GenBank Accession No. BF475237 "ESTsub2G9(96) Subtracted rice sperm cells cDNA Library *Oryza sativa* Indica Group cDNA, mRNA sequence." (2000).
U.S. Appl. No. 60/828,042, filed Sep. 28, 2006.
EPO Patent Application No. 06020370.0 filed Oct. 3, 2006.
Perez et al., "Factors affecting double-strand break-induced homologous recombination in mammalian cells," BioTechniques, 39:109-115, (Jul. 2005).

* cited by examiner

*Primary Examiner* — Li Zheng
(74) *Attorney, Agent, or Firm* — Hunton & Williams LLP

(57) ABSTRACT

Methods and means are provided for the exact exchange in eukaryotic cells, such as plant cells, of a target DNA sequence for a DNA sequence of interest through homologous recombination, whereby the selectable or screenable marker used during the homologous recombination phase for temporal selection of the gene replacement events can subsequently be removed without leaving a foot-print employing a method for the removal of a selected DNA flanked by two nucleotide sequences in direct repeats.

22 Claims, 5 Drawing Sheets

Continuation from Fig 2A
↓ Cross with receptor plant
↓ Selection of progeny for presence of SGM2
↓ Screening of progeny for absence of SGM1
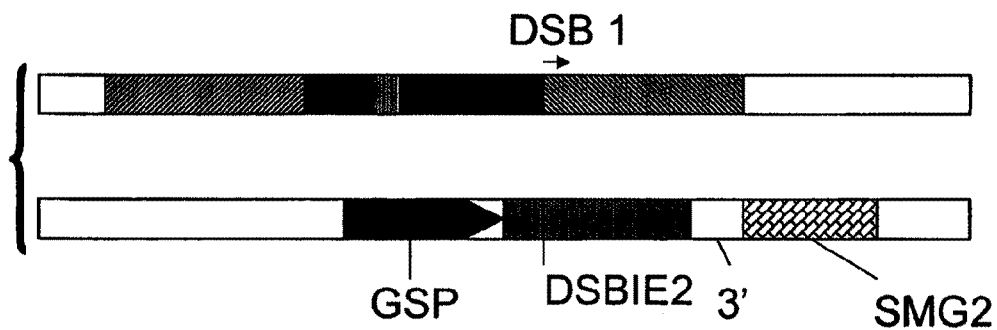
FIG 1B
↓ Cross with receptor plant
↓ Screening of progeny for absence of SGM2
↓ DSB 1

Continuation from Fig 2A
↓ Cross with receptor plant
↓ Selection of progeny for presence of SGM2
↓ Screening of progeny for absence of SGM1
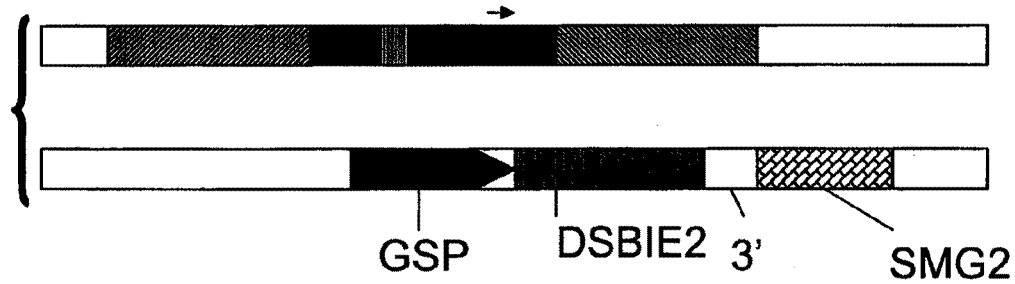
↓ Cross with receptor plant
↓ Screening of progeny for absence of SGM2
FIG 2B
↓ DSB 1

METHODS AND MEANS FOR EXACT REPLACEMENT OF TARGET DNA IN EUKARYOTIC ORGANISMS

CROSS-REFERENCE TO RELATED APPLICATIONS

This application is the U.S. National Stage filing of International Application No. PCT/EP2008/004524, filed Jun. 3, 2008, which claims priority to EP 070 109 98.8, filed Jun. 5, 2007, and U.S. Provisional Patent Application No. 60/933,814, filed Jun. 8, 2007, the disclosures of each of which are hereby incorporated by reference.

FIELD OF THE INVENTION

The current invention relates to improved methods and means for the exact exchange of a target DNA sequence for a DNA sequence of interest through homologous recombination in eukaryotic cells and organism, such as plant cells and plants, whereby the selectable or screenable marker used during the homologous recombination phase for temporal selection of the gene replacement events can subsequently be removed without introducing any other sequence variations.

BACKGROUND ART

Homologous recombination allows numerous targeted genetic modifications in prokaryotic and selected eukaryotic organisms including selected deletions, insertions or replacements.

In higher eukaryotic organisms, homologous recombination may be stimulated through the induction of double stranded DNA breaks via rare-cutting endonucleases, such as e.g. I-SceI.

WO2004/067753 describes the use of meganucleases for inducing homologous recombination ex vivo and in toto in vertebrate somatic tissues and the application thereof for genome engineering and gene therapy.

WO2000/46386 describes methods of modifying, repairing, attenuating and inactivating a gene or other chromosomal DNA in a cell through I-SceI induced double stranded breaks. Also disclosed are methods of treating or phrophylaxis of a genetic disease in an individual in need thereof.

In plants, induction of double stranded DNA breaks using I-SceI has been shown to increase the frequency of homologous recombination by at least two orders of magnitude using Agrobacteria to deliver the repair DNA to the plant cells (Puchta et al., 1996, Proc. Natl. Acad. Sci. U.S.A., 93, pp 5055-5060). Chilton and Que (2003, Plant Physiol. 133: pp 956-965) and Tzifira et al. (2003, Plant Physiol. 133: pp 1011-1023) report that T-DNA preferentially integrates in double stranded DNA breaks, artificially induced by the rare-cleaving enzymes I-SceI or I-CeuI. The reports also included donor T-DNA vectors which comprised a recognition site for the respective rare-cleaving enzyme.

In addition, methods have been described which allow the design of rare cleaving endonucleases to alter substrate or sequence-specificity of the enzymes, thus allowing to induce a double stranded break at virtually any locus of interest without being dependent on the presence of a recognition site for any of the natural rare-cleaving endonucleases. Briefly, chimeric restriction enzymes can be prepared using hybrids between a zinc-finger domain designed to recognize a specific nucleotide sequence and the non-specific DNA-cleavage domain from a natural restriction enzyme, such as FokI. Such methods have been described e.g. in WO 03/080809, WO94/18313 or WO95/09233 and in Isalan et al., 2001, Nature Biotechnology 19, 656-660; Liu et al. 1997, Proc. Natl. Acad. Sci. USA 94, 5525-5530). Another way of producing custom-made meganucleases, by selection from a library of variants, is described in WO2004/067736. Custom made meganucleases with altered sequence specificity and DNA-binding affinity may also be obtained through rational design as described in WO2007/047859.

WO2007/049095 describes "LADGLIDADG" homing endonuclease variants having mutations in two separate subdomains, each binding a distinct part of a modified DNA target half site, such that the endonuclease variant is able to cleave a chimeric DNA target sequence comprising the nucleotides bound by each subdomain.

WO2007/049156 and WO 2007/093836 describe I-CreI homing endonuclease variants having novel cleavage specificity and uses thereof.

WO2007/047859 describes rationally designed meganucleases with altered sequence specificity and DNA binding affinity.

WO2006/105946 described a method for the exact exchange in plant cells and plants of a target DNA sequence for a DNA sequence of interest through homologous recombination, whereby the selectable or screenable marker used during the homologous recombination phase for temporal selection of the gene replacement events can subsequently be removed without leaving a foot-print and without resorting to in vitro culture during the removal step, employing the therein described method for the removal of a selected DNA by microspore specific expression of a double stranded break inducing rare cleaving endonuclease.

U.S. provisional patent application 60/828,042 and European patent application 06020370.0, and WO2008/037436 describe variants of the methods and means of WO2006/105946 wherein the removal step of a selected DNA fragment induced by a double stranded break inducing rare cleaving endonuclease is under control of a germline-specific promoter. Other embodiments of the method relied on non-homologous endjoining at one end of the repair DNA and homologous recombination at the other end.

Some of the embodiments of the above identified methods and means for exact exchange of a target DNA fragment for a DNA fragment of interest require that the introduced repair DNA is introduced in the plant cell in the presence of the double stranded break inducing enzyme. The repair DNA normally also contains the preselected site recognized by a double stranded break inducing rare cleaving endonuclease and therefore the repair DNA is also prone to DNA cleavage. Accordingly, the efficiency of DNA insertion by homologous recombination may be lowered. To avoid this decrease in efficiency, the preselected site in the repair DNA may be altered in such a way that it is no longer recognized by the double stranded break inducing rare cleaving endonuclease. However, this entails the introduction of an extra change in the repair DNA compared to the target DNA in addition to the desired change.

The current invention provides an alternative solution to this problem, which does not require the modification of the preselected site in the repair DNA and consequently allows the exchange of the target DNA with only the desired nucleotide change, without modification of the preselected site. These and other problems are solved as described hereinafter in the different detailed embodiments of the invention, as well as in the claims.

SUMMARY OF THE INVENTION

In one embodiment of the invention, a method is provided for exchanging a target DNA sequence in the genome a eukaryotic cell or eukaryotic organism for a DNA sequence of interest comprising the following steps:

a. Inducing a first double stranded DNA break at a preselected site in the genome of a cell of the eukaryotic organism, the preselected site being located within the target DNA sequence or in the vicinity of the target DNA sequence and the preselected site being recognized by a first double-stranded break inducing (DSBI) enzyme;

b. Introducing a repair DNA molecule into the eukaryotic cell, the repair DNA molecule comprising i. a DNA sequence of interest located between two flanking DNA regions having at least 80% sequence homology to a DNA region flanking the target DNA sequence, and preferably flanking the preselected site in the genome of the eukaryotic cell;

ii. A selectable or screenable marker gene located between the flanking DNA regions, the selectable or screenable marker gene further being located between a first repeat sequence consisting of the 5'-terminal part of the preselected site and a second sequence consisting of the 3' terminal part of the preselected site, whereby the sequences common between the first and second repeat sequences are in direct repeat; and iii. At least one recognition site for a second DSBI enzyme located between the one of the flanking DNA regions and the first and second repeat sequence, preferably between the first and sequence direct repeat sequence;

c. Selecting a population of cells comprising the selectable or screenable marker;

d. Selecting a cell wherein the selectable or screenable marker has been introduced by homologous recombination through the flanking DNA regions;

e. Introducing a double stranded break at the recognition site for the second DSBI enzyme in the cell;

f. Selecting a progeny cell wherein the selectable or screenable marker gene is deleted by homologous recombination between the direct repeats thereby recreating the preselected site.

In another embodiment of the invention, a method is provided for exchanging a target DNA sequence in the genome, particularly the nuclear genome, of a plant for a DNA sequence of interest comprising the following steps:

a) Inducing a first double stranded DNA break at a preselected site in the genome of a cell of the plant, the preselected site being located within the target DNA sequence or in the vicinity of the target DNA sequence and the preselected site being recognized by a first double-stranded break inducing (DSBI) enzyme b) Introducing a repair DNA molecule into the eukaryotic cell, the repair DNA molecule comprising i) The DNA sequence of interest located between two flanking DNA regions having at least 80% sequence homology to a DNA region flanking the target DNA sequence, and preferably flanking the preselected site in the genome of the eukaryotic cell;

ii) A selectable or screenable marker gene located between the flanking DNA regions, the selectable or screenable marker gene further being located between a first repeat sequence consisting of the 5'-terminal part of the preselected site and a second sequence consisting of the 3' terminal part of the preselected site, whereby the sequences common between the first and second repeat sequences are in direct repeat; and iii) At least one recognition site for a second DSBI enzyme located between the one of the flanking DNA regions and the first and second repeat sequence;

c) Selecting a population of plant cells comprising the selectable or screenable marker;

d) Selecting a plant cell wherein the DNA sequence of interest (and the selectable or screenable marker) has been introduced by homologous recombination through the flanking DNA regions, and regenerating a plant from the plant cell;

e) Crossing the regenerated plant or a progeny plant thereof comprising the selectable marker gene with a plant comprising a rare cleaving double stranded break inducing ("DSBI") enzyme encoding chimeric gene, the chimeric gene comprising the following operably linked DNA segments:

i. a germline specific promoter;

ii. a DNA region encoding a double stranded DNA break inducing enzyme recognizing the recognition site located in the DNA of interest (i.e. the second double stranded DNA break inducing enzyme);

iii. a transcription termination and polyadenylation region;

f) Selecting a progeny plant (F1-plant) comprising the selectable or screenable marker gene and the DSBI enzyme encoding chimeric gene;

g) Crossing the progeny plant with another plant whereby the progeny plant is used as pollen donor;

h) Selecting a population of progeny plants (F2-population) which comprises the DSBI enzyme encoding chimeric gene; and i) Selecting a progeny plant wherein the selectable or screenable marker gene is deleted by homologous recombination between the first and second direct repeat sequence.

The invention relates to the eukaryotic cells and plants obtainable by the above described methods.

BRIEF DESCRIPTION OF THE DRAWINGS

FIG. 1 is a schematic representation of a method allowing exact replacement of a target DNA sequence with a replacement DNA sequence. DSB1: recognition site for a first double stranded break inducing enzyme; FS1: flanking sequence 1; FS2: flanking sequence 2; DSB2: recognition site for a second double stranded break inducing enzyme; SMG1: selectable marker gene 1 or screenable marker gene 1; SMG2: selectable marker gene 2 or screenable marker gene 2; DSBIE: double stranded break inducing enzyme; dr1: direct repeat sequence 1 contained within the 5' part of the preselected site recognized by DSBIE 1; dr2: direct repeat sequence 2 contained within the 5' part of the preselected site recognized by DSBIE1; GSP: germline specific promoter; 3': transcription termination and polyadenylation signal. In FIG. 1, the preselected site is located in the vicinity of the target DNA.

FIG. 2 is a schematic representation of a method allowing exact replacement of a target DNA sequence with a replacement DNA sequence similar to the method illustrated in FIG. 1. In this embodiment, the preselected site is located within the target DNA.

DETAILED EMBODIMENTS OF THE INVENTION

Figure 1A:
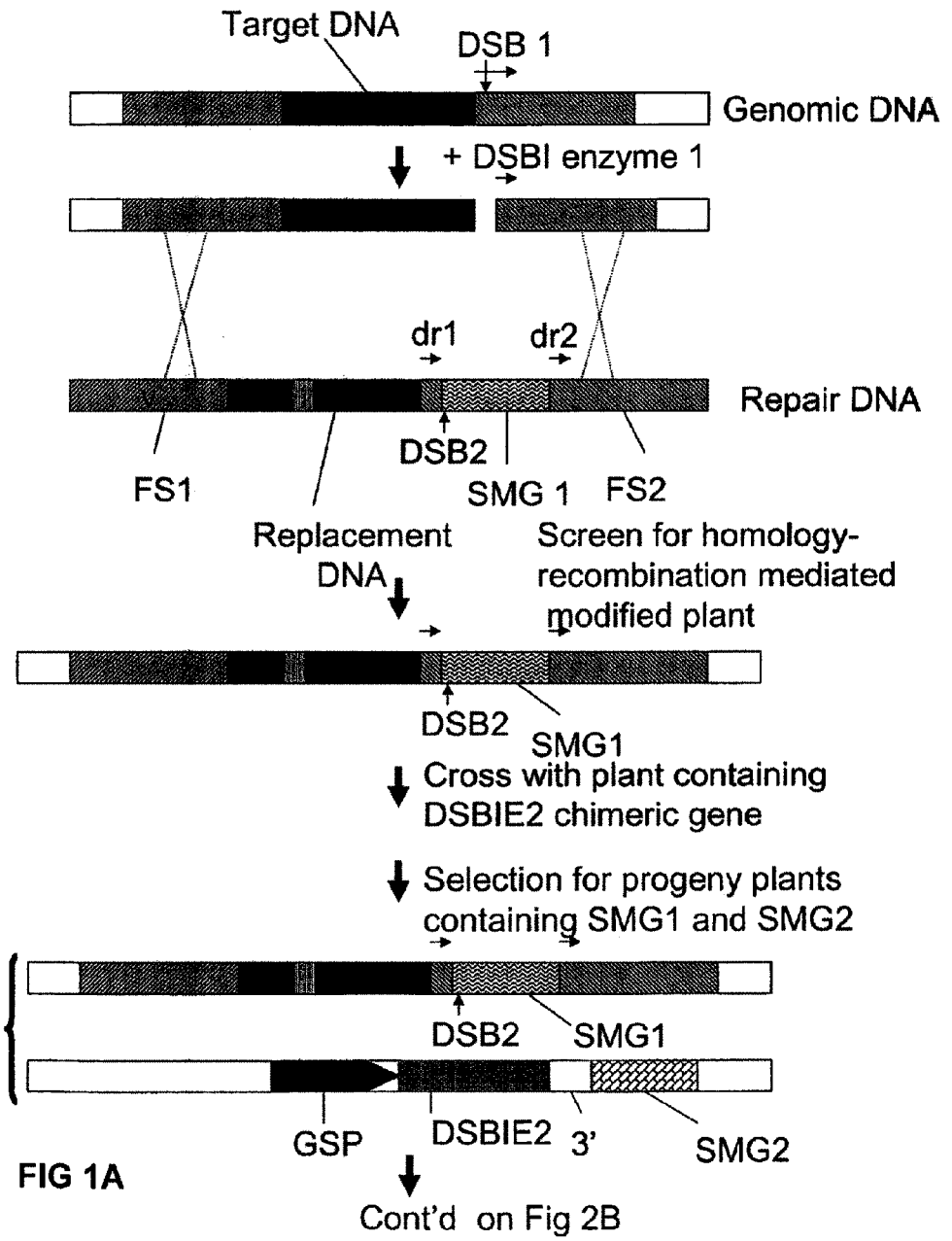
FIGS. 1 and 2 represent different embodiments of the method to exchange a target DNA for a DNA of in a plant cell without any additional modifications. These figures are for illustration purposes only and should not be used to construe the claims in a limiting manner.
Figure 2A:
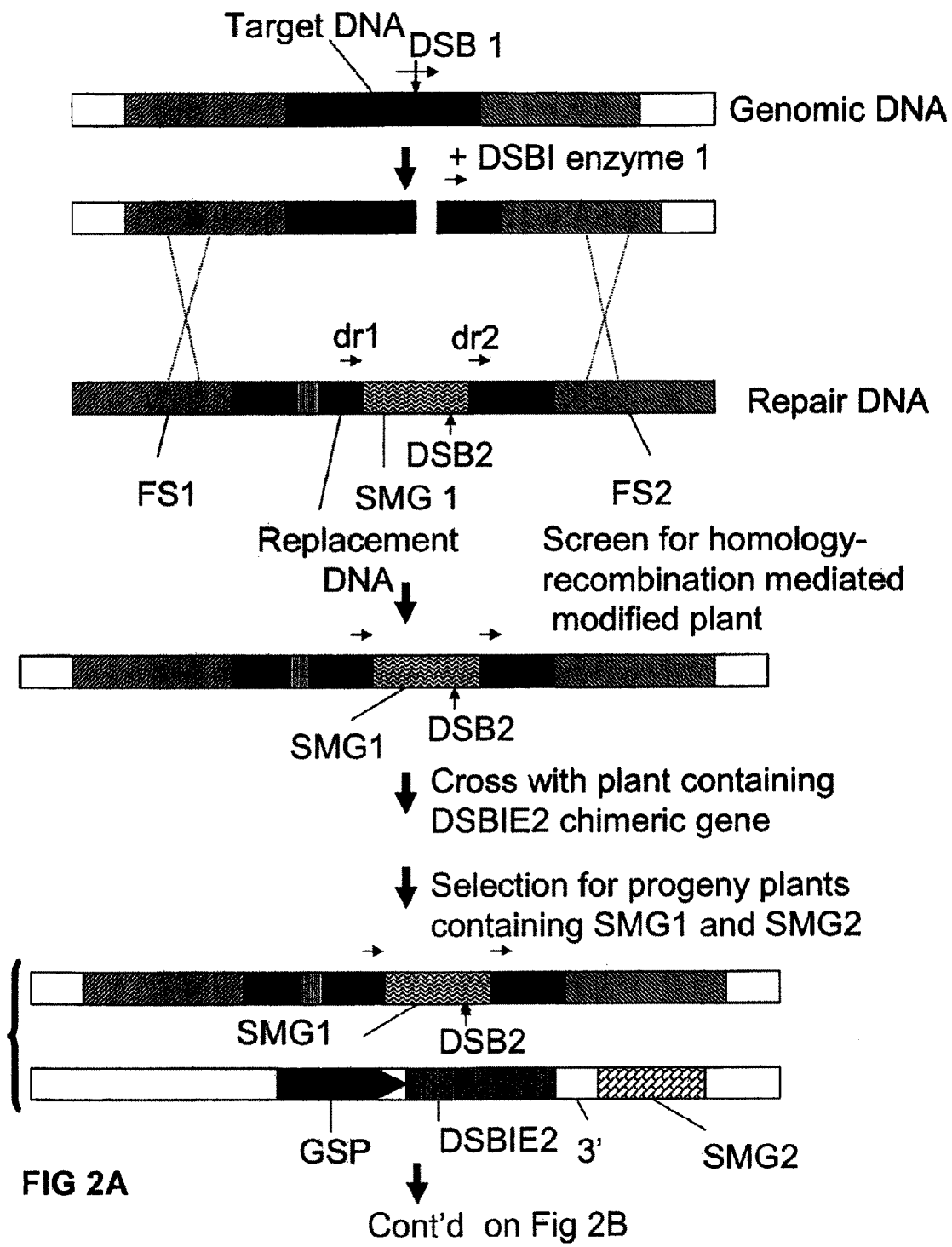

The current invention is based on the realization that the efficiency of several of the methods described e.g. in WO2006/105946 (particularly for the embodiments relying homologous recombination on both sides of the repair DNA) can be enhanced by providing a specific repair DNA wherein the direct DNA repeat (used in the removal step of the screenable or selectable marker) consist on the one end of the 5'-terminal part of the preselected site (recognized by the first double stranded break inducing enzyme) and on the other hand of the 3' terminal part of the preselected site. In this way the repair DNA does not contain a preselected site prone to cleavage by the first double stranded break inducing enzyme. However, upon induction of homologous recombination between the nucleotide sequences common to the 5' terminal and 3' terminal part of the preselected site in direct repeat (which results in the removal of the intermittent selectable or screenable marker gene), the original nucleotide sequence of the preselected site is reconstructed.

Thus, in a first embodiment, the invention provides a method for exchanging a target DNA sequence in the genome, particularly the nuclear genome, of a plant for a DNA sequence of interest comprising the following steps:
  a) Inducing a first double stranded DNA break at a preselected site in the genome of a cell of the plant, the preselected site being located within the target DNA sequence or in the vicinity of the target DNA sequence and the preselected site being recognized by a first double-stranded break inducing (DSBI) enzyme
  b) Introducing a repair DNA molecule into the plant cell, the repair DNA molecule comprising
    i) The DNA sequence of interest located between two flanking DNA regions having at least 80% sequence homology to a DNA region flanking the target DNA sequence, and preferably flanking the preselected site in the genome of the eukaryotic cell;
    ii) A selectable or screenable marker gene located between the flanking DNA regions, the selectable or screenable marker gene further being located between a first repeat sequence consisting of the 5'-terminal part of the preselected site and a second sequence consisting of the 3' terminal part of the preselected site, whereby the sequences common between the first and second repeat sequences are in direct repeat; and
    iii) At least one recognition site for a second DSBI enzyme located between the one of the flanking DNA regions and the first and second repeat sequence;
  c) Selecting a population of plant cells comprising the selectable or screenable marker;
  d) Selecting a plant cell wherein the DNA sequence of interest (and the selectable or screenable marker) has been introduced by homologous recombination through the flanking DNA regions, and regenerating a plant from the plant cell;
  e) Crossing the regenerated plant or a progeny plant thereof comprising the selectable marker gene with a plant comprising a rare cleaving double stranded break inducing ("DSBI") enzyme encoding chimeric gene, the chimeric gene comprising the following operably linked DNA segments:
    iv. a germline specific promoter, such as a microspore specific promoter;
    v. a DNA region encoding a double stranded DNA break inducing enzyme recognizing the recognition site located in the DNA of interest;
    vi. a transcription termination and polyadenylation region;
  f) Selecting a progeny plant (F1-plant) comprising the selectable or screenable marker gene and the DSBI enzyme encoding chimeric gene;
  g) Crossing the progeny plant with another plant whereby the progeny plant is used as pollen donor if the germline specific promoter is a promoter expressed during microsporogenesis or whereby the progeny plant is used as a pollen acceptor if the germline specific promoter is a promoter expressed during macrosporogenesis;
  h) Selecting a population of progeny plants (F2-population) which comprises the DSBI enzyme encoding chimeric gene; and
  i) Selecting a progeny plant wherein the selectable or screenable marker gene is deleted by homologous recombination between the one of the flanking DNA regions and a partial flanking DNA region comprising part of the one of the flanking DNA regions.

As used herein, a "double stranded DNA break inducing rare-cleaving endonuclease" is an enzyme capable of inducing a double stranded DNA break at a particular nucleotide sequence, called the "recognition site". Rare-cleaving endonucleases, also sometimes called mega-nucleases have a recognition site of 14 to 40 consecutive nucleotides. Therefore, rare-cleaving endonucleases have a very low frequency of cleaving, even in the larger plant genomes. Homing endonucleases constitute a family of such rare-cleaving endonucleases. They may be encoded by introns, independent genes or intervening sequences, and present striking structural and functional properties that distinguish them from the more classical restriction enzymes, usually from bacterial restriction-modification Type II systems. Their recognition sites have a general asymmetry which contrast to the characteristic dyad symmetry of most restriction enzyme recognition sites. Several homing endonucleases encoded by introns or inteins have been shown to promote the homing of their respective genetic elements into allelic intronless or inteinless sites. By making a site-specific double strand break in the intronless or inteinless alleles, these nucleases create recombinogenic ends, which engage in a gene conversion process that duplicates the coding sequence and leads to the insertion of an intron or an intervening sequence at the DNA level.

A well characterized homing endonuclease is I-SceI. I-SceI is a site-specific endonuclease, responsible for intron mobility in mitochondria in *Saccharomyces cerevisea*. The enzyme is encoded by the optional intron Sc LSU.1 of the 21S rRNA gene and initiates a double stranded DNA break at the intron insertion site generating a 4 by staggered cut with 3'OH overhangs. The recognition site of I-SceI endonuclease extends over an 18 by non-symmetrical sequence (Colleaux et al. 1988 *Proc. Natl. Acad. Sci. USA* 85: 6022-6026). The amino acid sequence for I-SceI and a universal code equivalent of the mitochondrial I-SceI gene have been provided by e.g. WO 96/14408. WO 96/14408 further discloses a number of variants of I-SceI protein which are still functional.

PCT application PCT/EP04/013122 (incorporated herein by reference) provides synthetic nucleotide sequence variants of I-SceI which have been optimized for expression in plants. The nucleotide sequence of such synthetic I-Sce I coding regions is set forth in SEQ ID No 1 in UIPAC code. The symbols of the UIPAC code have their usual meaning i.e. N=A or C or G or T; R=A or G; Y=C or T; B=C or G or T (not A); V=A or C or G (not T); D=A or G or T (not C); H=A or C or T (not G); K=G or T; M=A or C; S=G or C; W=A or T.

A list of other rare cleaving DSB inducing enzymes and their respective recognition sites is provided in Table I of WO 03/004659 (pages 17 to 20) (incorporated herein by reference). These include I-Sce I, I-Chu I, I-Dmo I, I-Cre I, I-Csm I, PI-Fli I, Pt-Mtu I, I-Ceu I, I-Sce II, I-Sce III, HO, PI-Civ I, PI-Ctr I, PI-Aae I, PI-BSU I, PI-DhaI, PI-Dra I, PI-Mav I, PI-Mch I, PI-Mfu I, PI-Mfl I, PI-Mga I, PI-Mgo I, PI-Min I, PI-Mka I, PI-Mle I, PI-Mma I, PI-Msh I, PI-Msm I, PI-Mth I, PI-Mtu I, PI-Mxe I, PI-Npu I, PI-Pfu I, PI-Rma I, PI-Spb I, PI-Ssp I, PI-Fac I, PI-Mja I, PI-Pho I, PI-Tag I, PI-Thy I, PI-Tko I or PI-Tsp I.

Furthermore, methods are available to design custom-tailored rare-cleaving endonucleases that recognize basically any target nucleotide sequence of choice. Briefly, chimeric restriction enzymes can be prepared using hybrids between a zinc-finger domain designed to recognize a specific nucleotide sequence and the non-specific DNA-cleavage domain from a natural restriction enzyme, such as FokI. Such methods have been described e.g. in WO 03/080809, WO94/18313 or WO95/09233 and in Isalan et al., 2001, *Nature Biotechnology* 19, 656-660; Liu et al. 1997, *Proc. Natl. Acad. Sci. USA* 94, 5525-5530). Another way of producing custom-made meganucleases, by selection from a library of variants, is described in WO2004/067736. Custom made meganucleases with altered sequence specificity and DNA-binding affinity may also be obtained through rational design as described in WO2007/047859

As used herein "a preselected site" indicates a particular nucleotide sequence in the plant nuclear genome, located in or near the target DNA sequence at which location it is desired to insert the foreign DNA or to exchange the target DNA sequence. A person skilled in the art would be able to either choose a double stranded DNA break inducing ("DSBI") enzyme recognizing the selected target nucleotide sequence or engineer such a DSBI endonuclease. Alternatively, a DSBI endonuclease recognition site may be introduced into the plant genome using any conventional transformation method or by conventional breeding using a plant line having a DSBI endonuclease recognition site in its genome, and any desired foreign DNA may afterwards be introduced into that previously introduced preselected target site.

The double stranded DNA breaks in the transforming DNA molecule may be induced conveniently by transient introduction of a plant-expressible chimeric gene comprising a plant-expressible promoter region operably linked to a DNA region encoding a double stranded break inducing enzyme. The DNA region encoding a double stranded break inducing enzyme may be a synthetic DNA region with plant-optimized codon usage. The endonuclease itself, as a protein, could also be introduced into the plant cells, e.g. by electroporation. However, the endonuclease can also be provided in a transient manner by introducing into the genome of a plant cell or plant, a chimeric gene comprising the endonuclease coding region operably linked to an inducible plant-expressible promoter, and providing the appropriate inducible compound for a limited time prior to, during or immediately after introduction of the transforming DNA molecule. The endonuclease could also be provided as an RNA precursor encoding the endonuclease.

The double stranded break inducing enzyme may comprise, but need not comprise, a nuclear localization signal (NLS), such as the NLS of SV40 large T-antigen [Raikhel, *Plant Physiol.* 100: 1627-1632 (1992) and references therein] [Kalderon et al. *Cell* 39: 499-509 (1984)]. The nuclear localization signal may be located anywhere in the protein, but is conveniently located at the N-terminal end of the protein. The nuclear localization signal may replace one or more of the amino acids of the double stranded break inducing enzyme.

As used herein, the "target DNA sequence" is the DNA sequence located in the genome of the plant cell which is modified, by addition, deletion or substitution.

As used herein "flanking DNA regions" are DNA sequences having homology to the DNA regions respectively upstream or downstream of the target DNA sequence. This allows to better control the insertion of the foreign DNA or the DNA molecule of interest. Indeed, integration by homologous recombination will allow precise joining of the foreign DNA fragment to the plant nuclear genome up to the nucleotide level.

The flanking DNA regions may vary in length, and should be at least about 10 nucleotides in length. However, the flanking region may be as long as is practically possible (e.g. up to about 100-150 kb such as complete bacterial artificial chromosomes (BACs)). Preferably, the flanking region will be about 50 bp to about 2000 bp. Moreover, the regions flanking the foreign DNA of interest need not be identical to the DNA regions flanking the preselected site and may have between about 80% to about 100% sequence identity, preferably about 95% to about 100% sequence identity with the DNA regions flanking the preselected site. The longer the flanking region, the less stringent the requirement for homology. Furthermore, it is preferred that the sequence identity is as high as practically possible in the vicinity of the location of exact insertion of the foreign DNA. Furthermore, to achieve exchange of the target DNA sequence without changing the DNA sequence of the adjacent DNA sequences, the flanking DNA sequences should preferably be identical to the DNA regions flanking the preselected site.

Moreover, the regions flanking the foreign DNA of interest need not have homology to the regions immediately flanking the preselected site, but may have homology to a DNA region of the nuclear genome further remote from that preselected site. Insertion of the foreign DNA will then result in a removal of the target DNA between the preselected insertion site and the DNA region of homology. In other words, the target DNA located between the homology regions will be substituted for the foreign DNA of interest.

Preferably, the preselected site and the further mentioned recognition sequence are recognized by different rare cleaving double stranded break inducing endonucleases.

Figure 3:
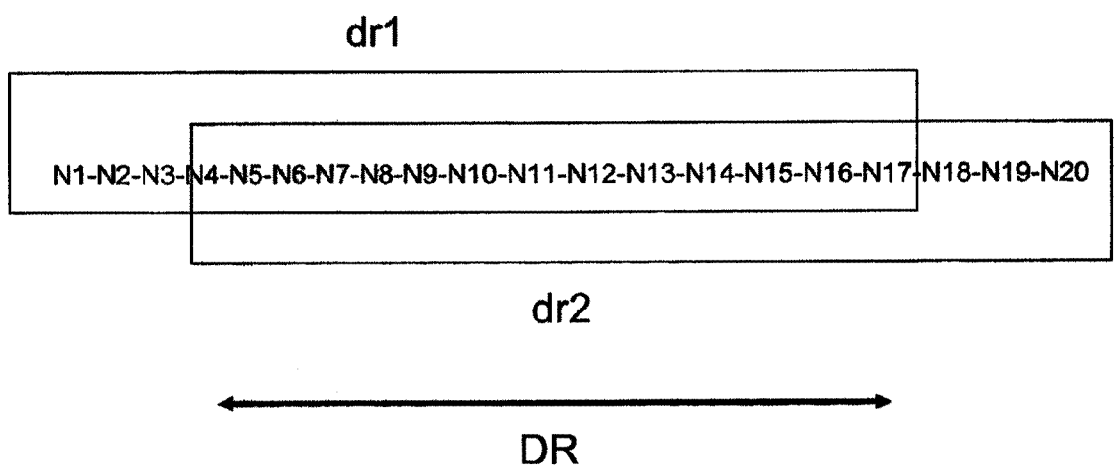
FIG. 3 is a schematic representation of a hypothetical 20 nucleotide long recognition site (N1-N20) for a double stranded break inducing rare cleaving enzyme. Indicated are a first and second repeat sequence as described elsewhere whereby dr1 corresponds to the 5' part of the recognition site (here exemplified as N1-N17) and dr2 corresponds to the 3' part of the recognition site (here exemplified as N4-N20). The direct repeat is between nucleotides N4 N17.

As used herein flanked by two DNA sequences "arranged in direct repeat" indicates that the sequence to be removed from the introduced DNA molecule is immediately preceded and followed by two DNA regions, one at each end, wherein the two DNA regions are essentially similar in nucleotide sequence. According to the invention, the DNA sequences arranged in direct repeat are a first DNA sequence upstream of the sequence to be removed (i.e. the selectable or screenable marker gene) consist of the 5' terminal part of the preselected site (i.e. the site selected by the first double stranded break inducing rare cleaving enzyme), whereas the second DNA sequence downstream of the sequence to be removed consists of the 3' terminal part of the preselected site. It will be immediately clear to the person skilled in the art that different preselected sites may differ in length and range e.g. from 15 nucleotides to 50 nucleotides. Accordingly, a sequence corresponding to the 5' terminal part of the preselected sequence is a sequence corresponding to the nucleotide sequence of the preselected sequence (or recognition site) which lacks at the 3' end of that sequence one or more nucleotides, such that the "5' terminal sequence" is no longer recognized and/or cleaved by the double stranded break inducing rare cleaving enzyme. Similarly, a sequence corresponding to the 3' terminal part of the preselected sequence is a sequence corresponding to the nucleotide sequence of the preselected sequence (or recognition site) which lacks at the 5' end of that sequence one or more nucleotides, such that the "3' terminal sequence" is no longer recognized and/or cleaved by the double stranded break inducing rare cleaving enzyme. 5' terminal part and 3' terminal part may lack 1, 2, 3, 4, 5, 6, 7, 8 or more nucleotides. Moreover, there is no need that there is a correspondence in the number of nucleotides lacking in the 5' terminal and 3' terminal part. E.g. while the 5' terminal part may be lacking 2 nucleotides of the recognition site at the 3' end, the 3' terminal part may be lacking 5 nucleotides of the recognition site at the 5' end. The actual sequences in direct repeat, which will allow removal of the nucleotide sequence located in-between, correspond to the nucleotide sequence common between the 5' terminal part and the 3' terminal part. Although the length of the actual direct repeat sequences will depend on the length of the recognition site or preselected site as well as on the amount of nucleotides lacking at respectively the 3' and 5' end, it is preferred that the nucleotide sequence in common comprises at least 5, or 10, or 14 or more nucleotides. Reference is made to FIG. 3 for a schematic representation of a 5' terminal part (dr1) and 3' terminal part of a hypothetical preselected site or recognition site.

It will be immediately clear to a person skilled in the art that for the purpose of the current invention that the repair DNA does not contain the preselected site. To this end, the selectable or screenable marker should preferably be immediately flanked by the direct repeat sequences or the 5' terminal part and 3' terminal parts of the preselected site. Preferably, one of the two sequences (5' terminal part or 3' terminal part) should be located in the repair DNA at its corresponding position with regard to the target DNA.

For avoidance of doubt, if the two DNA regions similar in nucleotide sequence are contained within a double stranded DNA molecule, these DNA sequences are to be located on the same DNA strand, in the same 5'→3' direction.

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e. a position in an alignment where a residue is present in one sequence but not in the other, is regarded as a position with non-identical residues. The alignment of the two sequences is performed by the Needleman and Wunsch algorithm (Needleman and Wunsch 1970) Computer-assisted sequence alignment, can be conveniently performed using standard software program such as GAP which is part of the Wisconsin Package Version 10.1 (Genetics Computer Group, Madison, Wis., USA) using the default scoring matrix with a gap creation penalty of 50 and a gap extension penalty of 3.

As used herein "located in the vicinity" refers to the DSBI being located at a distance of between 500 bp, 1 kbp to 10 kbp from the reference DNA sequence.

According to the current invention, at least one recognition site for a second double stranded break inducing rare cleaving enzyme is located between the direct repeats. In case where two such recognition sites are present, such recognition sites or parts thereof may be present in direct repeats and homologous recombination between two such sites or subparts thereof may remove the selectable or screenable marker. Upon such homologous recombination however an intact recognition site for the second double stranded break inducing rare cleaving enzyme is generated, and the first and second direct repeat sequences which are part of the preselected site are brought in closer contact via the deletion of the intervening sequences. Such a constellation of direct repeat sequences in close vicinity, flanking a recognition site for a double stranded break inducing enzyme is beneficial to induce high efficient recombination between the two direct repeat sequences deleting the remaining intervening sequences.

The methods described herein for the use in plants can be conveniently carried out, using a chimeric gene encoding a rare-cleaving double stranded break inducing enzyme, whereby the coding region for the endonuclease is under control of a germline specific promoter fragment.

As used herein, a "germline-specific promoter" is a promoter region, promoter or fragment which can promote transcription selectively, preferably specifically in plant cells that ultimately produce the gametes starting from megaspore-mother cell or the meiocyte. A germline-specific promoters as defined herein thus include gametophyte-specific promoter, gamete-specific promoters, promoters which control expression in microspores and/or megaspores or in their respective immediate precursor cells.

As used herein, a "promoter specific for gametogenesis" is a promoter region, promoter or fragment which can promote transcription selectively, preferably specifically in plant cells which are the immediate precursor cells of the gametes.

In angiosperm plants, sexual reproduction requires the production of viable male and female gametophytes. Pollen, as the male gametophyte is formed within the anther and is initiated from sporogenous cells, which develop into meiocytes. The meiocyte undergoes meiosis to form a tetrad of haploid microspores, which are subsequently released into the anther locule. Following expansion and vacuolation, an asymmetrical mitosis of the microspore results in bicellular pollen, containing a vegetative and a generative cell. In the majority of species, pollen is shed in bicellular condition. The female gametophyte, the embryo sac, initiates in the ovary from the megaspore mother cell or megasporocyte through two meiotic divisions, resulting in the formation of a linear tetrad of haploid megaspores. The chalazal megaspore enlarges in the preparation for the first mitotic division in the female gametophyte development, while the other three megaspores degenerate. Mitotic divisions occur in three generations of nuclei so that an eight nucleate embryo sac is formed. During these divisions the former megaspore cell enlarges and becomes much vacuolated. The eight-nucleate cell is organized into the seven-celled embryo sac through the delimitation by cell walls of six of the nuclei and associated cytoplasm. The three cells at the micropylar end constitute the egg apparatus which is composed of the egg and two synergids. At the opposite end of the embryo sac are three antipodal cells. Between the two groups of cells is the large central cell containing two polar nuclei, which may fuse prior to fertilization and form the diploid secondary endosperm nucleus.

As used herein "a microspore specific promoter region" or "a microspore specific promoter" or a "a microspore specific promoter fragment" is a promoter region or promoter or promoter fragment which can promote transcription selectively, preferably specifically, in the unicellular microspore of a plant. A suitable microspore specific promoter region is described in WO 97/30166 (incorporated herein by reference) as the promoter region from NTM19 gene in tobacco and its use in a method for targeted exchange in plants is exemplified in WO2006/105946.

As used herein "a megaspore specific promoter region" or "a megaspore specific promoter" or a "a megaspore specific promoter fragment" is a promoter region or promoter or promoter fragment which can promote transcription selectively, preferably specifically, in a unicellular megaspore of a plant, preferably a megaspore which develops into an embryo sac.

Particular promoters such as the BnSKP1γ1 may control transcription specifically or selectively both in microspores and megaspores of plants (Drouad et al. 2000 Sex Plant Reprod. 13: 29-35).

Further suitable germline-specific promoters exemplified in U.S. provisional patent application 60/828,042 and European patent application 06020370.0 may be any one of the following (citations below are herein incorporated by reference):

i. A promoter comprising an *Arabidopsis* egg apparatus (EA) specific enhancer, fused to a minimal promoter element such as a minimal 35S promoter, as described by Yang et al., 2005, Plant Physiol. 139(3):1421-1432 ii. An Arabidopsis TAG1 promoter as described by Galli et al., 2003 Genetics. 165(4):2093-2105 (expressed in male and female gametophytes)

iii. An Arabidopsis Duo1 promoter (male generative cell and sperm cell activity as described by Rotman et al., 2005 Curr Biol. 15(3):244-248 iv. promoters as could be isolated from the female gametophytic genes described by Yu et al., 2005 Plant Physiology 139(4):1853-1869 v. a promoter from LGC1 from *Lilium* expressed in male generative cell and sperm cells (Xu to al., 1999 Proc Natl Acad Sci USA 96(5):2554-2558; Singh et al. 2003 FEBS Lett. 2003 542(1-3):47-52.

vi. A promoter from the ERCC1 homolog expressed in male sperm cells (Xu et al. 1998 Plant J. 13(6):823-829)

vii. A promoter from H2A or H3 histone genes (Xu et al. 1999 Male gametic cell-specific expression of H2A and H3 histone genes. Plant Molecular Biology 39, 607-614; Okada et al. (2005) Transcriptional activity of male gamete-specific histone gcH3 promoter in sperm cell of *Lilium longiflorum*. Plant and Cell Physiology 46, 797-802)

viii. Promoters from sperm cell genes as identified in rice (Chen, Schuan University, GenBank entries BE225314 to BE225323, BF475189 to BF475237) and as identified in corn (Engel et al., 2003 The Plant Journal 34: 697-707)

ix. The Zmea1 promoter (Marton et al. Science. 2005, 307:573-576) and Zmes promoters (Cordts et al. Plant J. 2001 25(1):103-114) specific for egg apparatus and embryosac, respectively x. Promoters comprising silencer elements recognized by GRSF or germline restrictive silencing factor (Haerizadeh et al. 2006 *Science* 28 313: pp. 496-499)

xi. BnM1 or BnM3.4 promoter described by Guerche et al. 1999 (Plant Molecular Biology 40: 857-872) and promoters driving expression of microspore-specific cDNAs M21.

As used herein "coding region for a rare cleaving double stranded break inducing endonuclease" or "coding region for a rare cleaving double stranded break inducing enzyme" is a nucleotide sequence which encodes a polypeptide that is characterized as a rare cleaving DSBI enzyme such as the homing endonucleases or the chimeric endonucleases described elsewhere in this application. The coding region may thus comprise any nucleotide sequence that encodes any of the amino acid sequences of the homing endonucleases listed in the following table, which can be found in public databases under the mentioned accession numbers (all herein incorporated by reference):

| DSBI enzyme | Accession number |
| --- | --- |
| I-AniI | P03880 |
| I-CvuI | P56347 |
| I-CreI | P05725 |
| I-ChuI | Q32001 |
| I-CpaI - I-CpaIII - I-CpaIV - I-CpaV | Q39562/Q8WKZ5/Q8WKZ6/Q8WKZ8 |
| I-CpaII | Q39559 |
| I-CeuI | P32761 |
| I-DmoI | P21505 |
| I-SceI | P03882 |
| I-SceII | P03878 |
| I-SceIII | Q9ZZX3 |
| PI-SceI | P17255 |
| I-NanI | Q25535 |
| I-NitI | Q25567 |
| I-NjaI | Q25568 |
| I-PpoI | Q94702 |
| PI-PfuI | O73954 |
| PI-PkoI | P77933 |
| PI-PkoII | P77933 |
| PI-PspI | Q51334 |
| PI-TfuI | P74918 |
| PI-TfuII | P74918 |
| PI-ThyI | Q9HH05 |
| PI-ThyII | Q9HH05 |
| PI-TliI | P30317 |
| PI-TliII | P30317 |
| I-TevI | P13299 |
| I-TevII | P07072 |
| I-TevIII | Q38419 |

It will be clear that for expression of the endonucleases under the control of a microspore specific promoter fragment, the coding region should be adapted so that the universal codon language is used to encode the above mentioned polypeptides. The coding region may further be optimized for expression in plants and the synthetic coding region may have a nucleotide sequence which has been designed to fulfill the following criteria:

a) the nucleotide sequence encodes a functional rare cleaving double stranded break inducing endonuclease, b) the nucleotide sequence has a GC content of about 50% to about 60% c) the nucleotide sequence does not comprise a nucleotide sequence selected from the group consisting of GATAAT, TATAAA, AATATA, AATATT, GATAAA, AATGAA, AATAAG, AATAAA, AATAAT, AACCAA, ATATAA, AATCAA, ATACTA, ATAAAA, ATGAAA, AAGCAT, ATTAAT, ATACAT, AAAATA, ATTAAA, AATTAA, AATACA and CATAAA;

d) the nucleotide does not comprise a nucleotide sequence selected from the group consisting of CCAAT, ATTGG, GCAAT and ATTGC;

e) the nucleotide sequence does not comprise a sequence selected from the group consisting of ATTTA, AAGGT, AGGTA, GGTA or GCAGG;

f) the nucleotide sequence does not comprise a GC stretch consisting of 7 consecutive nucleotides selected from the group of G or C;

g) the nucleotide sequence does not comprise a GC stretch consisting of 5 consecutive nucleotides selected from the group of A or T; and h) the nucleotide sequence does not comprise codons coding for Leu, Ile, Val, Ser, Pro, Thr, Ala that comprise TA or CG duplets in positions 2 and 3 (i.e. the nucleotide sequence does not comprise the codons TTA, CTA, ATA, GTA, TCG, CCG, ACG and GCG).

The double stranded break inducing enzyme may comprise, but need not comprise, a nuclear localization signal (NLS) [Raikhel, *Plant Physiol.* 100: 1627-1632 (1992) and references therein], such as the NLS of SV40 large T-antigen [Kalderon et al. *Cell* 39: 499-509 (1984)]. The nuclear localization signal may be located anywhere in the protein, but is conveniently located at the N-terminal end of the protein. The nuclear localization signal may replace one or more of the amino acids of the double stranded break inducing enzyme.

Having understood the underlying principles of the current invention, a person skilled in the art will realize that the method can be used in cells of eukaryotic organisms different from plants.

Thus, in another embodiment of the invention, a method is provided for exchanging a target DNA sequence in the genome a eukaryotic cell or eukaryotic organism for a DNA sequence of interest comprising the following steps:

g. Inducing a first double stranded DNA break at a preselected site in the genome of a cell of the eukaryotic organism, the preselected site being located within the target DNA sequence or in the vicinity of the target DNA sequence and the preselected site being recognized by a first double-stranded break inducing (DSBI) enzyme;

h. Introducing a repair DNA molecule into the eukaryotic cell, the repair DNA molecule comprising
  i. The DNA sequence of interest located between two flanking DNA regions having at least 80% sequence homology to a DNA region flanking the target DNA sequence, and preferably flanking the preselected site in the genome of the eukaryotic cell;
  ii. A selectable or screenable marker gene located between the flanking DNA regions, the selectable or screenable marker gene further being located between a first repeat sequence consisting of the 5'-terminal part of the preselected site and a second sequence consisting of the 3' terminal part of the preselected site, whereby the sequences common between the first and second repeat sequences are in direct repeat; and
  iii. At least one recognition site for a second DSBI enzyme located between the one of the flanking DNA regions and the first and second repeat sequence;

i. Selecting a population of cells comprising the selectable or screenable marker;

j. Selecting a cell wherein the selectable or screenable marker has been introduced by homologous recombination through the flanking DNA regions;

k. Introducing a double stranded break at the recognition site for the second DSBI enzyme in the cell;

l. Selecting a progeny cell wherein the selectable or screenable marker gene is deleted by homologous recombination between the direct repeats thereby recreating the preselected site.

The terms herein defined with regard to their meaning in plant cells, can be applied mutatis mutandis to apply to eukaryotic cells, particularly higher eukaryotic cells such as vertebrates, animals, mammals in general.

It will also be clear that the terms used to describe the method such as "introduction of a DNA fragment" as well as "regeneration of a plant from the cell" do not imply that such DNA fragment necessarily needs to be introduced by transformation techniques. Indeed, it will be immediately clear to the person skilled in the art that the DNA molecule of interest may also be introduced by breeding or crossing techniques from one plant to another.

However, it will be clear that the DNA molecule of interest may be introduced into the plant cells by any method known in the art, including Agrobacterium mediated transformation but also by direct DNA transfer methods. The transforming DNA molecule can be transferred into plant cells using any conventional method, including but not limited to direct DNA transfer method. As used herein "direct DNA transfer" is any method of DNA introduction into plant cells which does not involve the use of natural *Agrobacterium* spp. and which is capable of introducing DNA into plant cells. This includes methods well known in the art such as introduction of DNA by electroporation into protoplasts, introduction of DNA by electroporation into intact plant cells or partially degraded tissues or plant cells, introduction of DNA through the action of agents such as PEG and the like, into protoplasts, use of silicon whiskers, and bombardment with DNA coated microprojectiles.

The DNA may be integrated by homologous recombination or non-homologous end-joining methods involving a double stranded break induction at a preselected site as described e.g. in PCT/EP04/013122.

"Selectable or screenable markers" as used herein have there usual meaning in the art and include, but are not limited to plant expressible phosphinotricin acetyltransferase, neomycine phosphotransferase, glyphosate oxidase, glyphosate tolerant EPSP enzyme, nitrilase gene, mutant acetolactate synthase or acetohydroxyacid synthase gene, β-glucoronidase (GUS), R-locus genes, green fluorescent protein and the likes.

The selection of the plant cell or plant wherein the selectable or screenable marker and the rest of the foreign DNA molecule has been introduced by homologous recombination through the flanking DNA regions can e.g. be achieved by screening for the absence of sequences present in the transforming DNA but located outside of the flanking DNA regions. Indeed, presence of sequences from the transforming DNA outside the flanking DNA regions would indicate that the transformed plant cells origination by random DNA insertion. To this end, selectable or screenable markers may be included in the transforming DNA molecule outside of the flanking DNA regions, which can then be used to identify those plant cells which do not have the selectable or screenable markers located outside of the transforming DNA and which may have arisen by homologous recombination through the flanking DNA regions. Alternatively, the transforming DNA molecule may contain selectable markers outside the flanking DNA regions that allow selection for the absence of such genes (negative selectable marker genes).

It will be appreciated that the means and methods of the invention may be used in any plant capable of reproduction through pollen or egg cells, including corn, tobacco, cereal plants including wheat, oat, barley, rye, rice, turfgrass, sorghum, millet or sugarcane plants. The methods of the invention can also be applied to any plant (Angiospermae or Gymnospermae) including but not limited to cotton, canola, oilseed rape, soybean, vegetables, potatoes, *Lemna* spp., *Nicotiana* spp., *Arabidopsis*, alfalfa, barley, bean, corn, cotton, flax, pea, rape, rice, rye, safflower, sorghum, soybean, sunflower, tobacco, wheat, asparagus, beet, broccoli, cabbage, carrot, cauliflower, celery, cucumber, eggplant, lettuce, onion, oilseed rape, pepper, potato, pumpkin, radish, spinach, squash, tomato, zucchini, almond, apple, apricot, banana, blackberry, blueberry, cacao, cherry, coconut, cranberry, date, grape, grapefruit, guava, kiwi, lemon, lime, mango, melon, nectarine, orange, papaya, passion fruit, peach, peanut, pear, pineapple, pistachio, plum, raspberry, strawberry, tangerine, walnut and watermelon.

It is also an object of the invention to provide plant cells and plants generated according to the methods of the invention. Gametes, seeds, embryos, either zygotic or somatic, progeny or hybrids of plants comprising the DNA insertion events, which are produced by traditional breeding methods are also included within the scope of the present invention. Such plants may contain a heterologous DNA sequence instead of a target sequence, and will only be different from their progenitor plants by the presence of this heterologous DNA or DNA sequence post exchange.

The plants obtained by the methods described herein may be further crossed by traditional breeding techniques with other plants to obtain progeny plants comprising the targeted DNA insertion events obtained according to the present invention.

The following non-limiting Examples describe the removal of a selected subfragment from an introduced DNA molecule using a double strand DNA break inducing enzyme, such as I-SceI, and direct repeats which are subfragments of an I-CeuI recognition site.

Unless stated otherwise in the Examples, all recombinant DNA techniques are carried out according to standard protocols as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Croy, jointly published by BIOS Scientific Publications Ltd (UK) and Blackwell Scientific Publications, UK. Other references for standard molecular biology techniques include Sambrook and Russell (2001) Molecular Cloning: A Laboratory Manual, Third Edition, Cold Spring Harbor Laboratory Press, NY, Volumes I and II of Brown (1998) Molecular Biology LabFax, Second Edition, Academic Press (UK). Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany.

Throughout the description and Examples, reference is made to the following sequences:

SEQ ID No 1: nucleotide sequence of synthetic I-SceI coding region (UIPAC code).

SEQ ID No 2: nucleotide sequence of synthetic I-SceI coding region.

SEQ ID No 3: nucleotide sequence of the I-SceI recognition site

SEQ ID No 4: nucleotide sequence of the I-CeuI recognition site

EXAMPLES

Using conventional recombinant DNA techniques a T-DNA vector is constructed comprising the following operably linked DNA fragments:
  a CaMV 35S promoter region
  a DNA region encoding the non-functional N-terminal part of screenable marker (e.g. β-glucuronidase)
  a DNA sequence consisting of the 5' terminal region of 22 nucleotides of the I-CeuI recognition site (SEQ ID No 4)
  a selectable marker gene (such as a plant-expressible phosphinotricin acetyltransferase)
  a I-SceI recognition site (SEQ ID No 3)
  a DNA sequence consisting of the 3' terminal region of 22 nucleotides of the I-CeuI recognition site
  a DNA region encoding the non-functional C-terminal part of the screenable marker (such that upon homologous recombination between the two I-CeuI derived repeat sequences a functional coding region for the screenable marker is generated).
  a 3' end region involved in transcription termination and polyadenylation.

The T-DNA is introduced in a tobacco plant cells, and transgenic plants are regenerated as conventional in the art. These transgenic tobacco plant lines can be used conveniently to determine whether homologous recombination occurs between the two subparts of the I-CeuI recognition site, resulting in a removal of the selectable marker gene and generation of an intact screenable marker.

Transgenic tobacco plants expressing I-SceI under control of the microspore specific promoter of the NTM19 linked to a neomycin resistance gene have been described in WO2006/105946. In a similar manner, transgenic tobacco plants expressing I-CeuI under control of the microspore specific promoter of the NTM19 gene are generated.

Transgenic plants containing the test-construct are crossed with transgenic tobacco plants expressing I-SceI under control of the microspore specific promoter of the NTM19 or with transgenic tobacco plants expressing I-CeuI under control of the microspore specific promoter of the NTM19, and progeny plants comprising both the test-construct and the chimeric I-SceI or I-CeuI region are identified. These plants are used as pollen donor to pollinate a non-transgenic plant. In the Progeny plants from the initial cross between transgenic plants containing the test-construct and I-CeuI expressing plants do not show an increased frequency of homologous recombination, whereas progeny plants from the initial cross between transgenic plants containing the test-construct and I-SceI expressing plants exhibit an increased frequency of homologous recombination.

To test whether homologous recombination can occur between short DNA sequences of 16 identical nucleotides in length, a T-DNA vector has been constructed which contains right and left T-DNA border sequences with in between the T-DNA borders a selectable chimeric gene comprising a nopaline synthase promoter, operably linked to a nptII coding region and a terminator region from the nopaline synthase gene and a further chimeric construct comprising in order:
  a. a constitutive promoter region
  b. a nucleotide sequence of 16 nucleotides
  c. a recognition site for I-SceI
  d. a DNA region encoding green fluorescent protein (GFP)
  e. a recognition site for I-SceI in inverted orientation with regard to the I-SceI site sub c)
  f. the same nucleotide sequence of 16 nucleotides as sub b)
  g. a DNA region encoding β-glucuronidase (GUS)
  h. a terminator region from the nopaline synthase gene Transgenic tobacco plants have been generated by leaf-disk transformation using Agrobacterium tumefaciens (EHA 105) comprising the above described T-DNA vector whereby selection was performed for kanamycin resistant plant cells.

As expected, no GUS expression was observed in leaves of transgenic plants, and four different transgenic TO lines with a clear GFP expression and no GUS expression were selected.

Leaf disks of the selected transgenic lines where subjected to Agrobacterium mediated transformation using a Agrobacterium strain comprising a T-DNA vector comprising a chimeric I-SceI coding region under control of a plant-expressible promoter and a selectable gene encoding phosphinotricin-resistance between the T-DNA borders. Selection is performed for phosphinotricin resistant plant cells.

From the selected plant cells, transgenic calli are obtained and plants are regenerated. Plant tissue and/or callus tissue are screened for GFP and GUS expression. In plants where a homologous recombination has occurred between the direct repeat sequence of 16 nucleotides, the coding region for GFP is deleted and the coding region for GUS is placed under control of the constitutive promoter. The plant material is accordingly negative for GFP expression and positive for GUS expression. From GFP negative, GUS positive plant material, the DNA fragment downstream of the constitutive promoter is amplified by PCR and the nucleotide sequence determined for determination whether homologous recombination occurred through the 16 nt direct repeat.

The invention claimed is:

1. A method for exchanging a target DNA sequence in the genome of a eukaryotic cell or eukaryotic organism for a DNA sequence of interest comprising the following steps:
   a. inducing a first double stranded DNA break at a preselected site in the genome of a cell of said eukaryotic organism, said preselected site being located within said target DNA sequence or within 1 kb of said target DNA sequence and said preselected site being recognized by a first double-stranded break inducing (DSBI) enzyme;
   b. introducing a repair DNA molecule into said eukaryotic cell, said repair DNA molecule comprising
      i. said DNA sequence of interest located between two flanking DNA regions of at least 10 nucleotides in length and having at least 80% sequence homology to a DNA region flanking said target DNA sequence, and preferably flanking said preselected site in the genome of said eukaryotic cell;
      ii. a selectable or screenable marker gene located between said flanking DNA regions, said selectable or screenable marker gene further being located between a first repeat sequence consisting of a 5'-terminal part of said preselected site and a second repeat sequence consisting of a 3' terminal part of said preselected site, whereby the sequences common between said first and second repeat sequences are in direct repeat and are more than 14 nucleotides in length; and
      iii. at least one recognition site for a second DSBI enzyme located between said one of the flanking DNA regions and said first and second repeat sequence;
   c. selecting a population of cells comprising said selectable or screenable marker;
   d. selecting a cell wherein said selectable or screenable marker has been introduced by homologous recombination through said flanking DNA regions;
   e. introducing a double stranded break at the recognition site for said second DSBI enzyme in said cell; and
   f. selecting a progeny cell wherein said selectable or screenable marker gene is deleted by homologous recombination between said direct repeats thereby recreating said preselected site.

2. The method of claim 1, wherein said first double stranded break at said preselected site is induced by introduction of a first DSBI enzyme, said first DSBI enzyme not recognizing said recognition site for said second DSBI enzyme located in said repair DNA.

3. The method of claim 1, wherein said first DSBI enzyme and said second DSBI enzyme are two different DSBI enzymes, wherein said DSBI enzymes are I-Sce I, I-Chu I, I-Dmo I, I-Cre I, I-Csm I, PI-Fli I, Pt-Mtu I, I-Ceu I, I-Sce II, I-Sce III, HO, PI-Civ I, PI-Ctr I, PI-Aae I, PI-BSU I, PI-DhaI, PI-Dra I, PI-May I, PI-Mch I, PI-Mfu I, PI-Mfl I, PI-Mga I, PI-Mgo I, PI-Min I, PI-Mka I, PI-Mle I, PI-Mma I, PI-Msh I, PI-Msm I, PI-Mth I, PI-Mtu I, PI-Mxe I, PI-Npu I, PI-Pfu I, PI-Rma I, PI-Spb I, PI-Ssp I, PI-Fac I, PI-Mja I, PI-Pho I, PI-Tag I, PI-Thy I, PI-Tko I, PI-Tsp I, a chimeric endonuclease comprising a Zn finger DNA binding domain and a DNA cleavage domain, or a custom meganuclease.

4. The method of claim 1, wherein said first DSBI enzyme is a custom meganuclease recognizing said preselected site.

5. The method of claim 1, wherein said second DSBI enzyme is I-SceI.

6. The method of claim 5, wherein said second DSBI enzyme is the enzyme encoded by the nucleotide sequence of SEQ ID No 1 or SEQ ID No 2.

7. The method of claim 1, wherein said eukaryotic cell is a plant cell or said eukaryotic organism is a plant.

8. A method for exchanging a target DNA sequence in the genome, particularly the nuclear genome, of a plant for a DNA sequence of interest comprising the following steps:
   a) inducing a first double stranded DNA break at a preselected site in the genome of a cell of said plant, said preselected site being located within said target DNA sequence or within 1 kb of said target DNA sequence and said preselected site being recognized by a first double-stranded break inducing (DSBI) enzyme;
   b) introducing a repair DNA molecule into said eukaryotic cell, said repair DNA molecule comprising
      i) said DNA sequence of interest located between two flanking DNA regions of at least 10 nucleotides in length and having at least 80% sequence homology to a DNA region flanking said target DNA sequence, and preferably flanking said preselected site in the genome of said eukaryotic cell;
      ii) a selectable or screenable marker gene located between said flanking DNA regions, said selectable or screenable marker gene further being located between a first repeat sequence consisting of a 5'-terminal part of said preselected site and a second repeat sequence consisting of a 3' terminal part of said preselected site, whereby the sequences common between said first and second repeat sequences are in direct repeat and are more than 14 nucleotides in length; and
  iii) at least one recognition site for a second DSBI enzyme located between said one of the flanking DNA regions and said first and second repeat sequence;
c) selecting a population of plant cells comprising the selectable or screenable marker;
d) selecting a plant cell wherein the DNA sequence of interest and the selectable or screenable marker has been introduced by homologous recombination through the flanking DNA regions, and regenerating a plant from the plant cell;
e) crossing the regenerated plant or a progeny plant thereof comprising the selectable marker gene with a plant comprising a rare cleaving double stranded break inducing ("DSBI") enzyme encoding chimeric gene, the chimeric gene comprising the following operably linked DNA segments:
  i. a germline specific promoter;
  ii. a DNA region encoding a double stranded DNA break inducing enzyme recognizing the recognition site located in the DNA of interest;
  iii. a transcription termination and polyadenylation region;
f) selecting an F1 progeny plant comprising the selectable or screenable marker gene and the DSBI enzyme encoding chimeric gene;
g) crossing the progeny plant with another plant whereby the progeny plant is used as pollen donor if said germline specific promoter is a microspore specific promoter and whereby said progeny plant is used as pollen acceptor or female plant if said germline specific promoter is a megaspore specific promoter;
h) selecting a population of F2 progeny plants which comprises the DSBI enzyme encoding chimeric gene; and
i) selecting a progeny plant wherein the selectable or screenable marker gene is deleted by homologous recombination between the first and second direct repeat sequence.

9. The method of claim 8, wherein said first double stranded break at said preselected site is induced by introduction of a first DSBI enzyme, said first DSBI enzyme not recognizing said recognition site for said second DSBI inducing enzyme located in said repair DNA.

10. The method of claim 8, wherein said first DSBI enzyme and said second DSBI enzyme are two different DSBI enzymes, wherein said DSBI enzymes are I-Sce I, I-Chu I, I-Dmo I, I-Cre I, I-Csm I, PI-Fli I, Pt-Mtu I, I-Ceu I, I-Sce II, I-Sce III, HO, PI-Civ I, PI-Ctr I, PI-Aae I, PI-BSU I, PI-DhaI, PI-Dra I, PI-May I, PI-Mch I, PI-Mfu I, PI-Mfl I, PI-Mga I, PI-Mgo I, PI-Min I, PI-Mka I, PI-Mle I, PI-Mma I, PI-Msh I, PI-Msm I, PI-Mth I, PI-Mtu I, PI-Mxe I, PI-Npu I, PI-Pfu I, PI-Rma I, PI-Spb I, PI-Ssp I, PI-Fac I, PI-Mja I, PI-Pho I, PI-Tag I, PI-Thy I, PI-Tko I, PI-Tsp I, a chimeric endonuclease comprising a Zn finger DNA binding domain and a DNA cleavage domain, or a custom meganuclease.

11. The method of claim 8, wherein said first DSBI enzyme is a custom meganuclease recognizing said preselected site.

12. The method of claim 8, wherein said second DSBI enzyme is I-SceI.

13. A DNA vector for exchanging a target DNA sequence in the genome of a plant cell for a DNA sequence of interest through the induction of a double stranded break at a preselected site within said target sequence or within 1 kb thereof, said DNA vector comprising
  a. said DNA sequence of interest located between two flanking DNA regions of at least 10 nucleotides in length and having at least 80% sequence homology to a DNA region flanking said target DNA sequence and flanking said preselected site;
  b. a selectable or screenable marker gene located between said flanking DNA regions, said selectable or screenable marker gene further being located between a first repeat sequence consisting of a 5'-terminal part of said preselected site and a second repeat sequence consisting of a 3' terminal part of said preselected site, whereby the sequences common between said first and second repeat sequences are in direct repeat and are more than 14 nucleotides in length; and
  c. a recognition site for a DSBI enzyme located between said one of the flanking DNA regions and said first and second repeat sequence.

14. The method of claim 1, wherein the sequences common between said first and second repeat sequences are 16 nucleotides in length.

15. The method of claim 1, wherein said DNA sequence of interest comprises between said first and second repeat sequence, two recognition sites for said second DSBI enzyme, said two recognition sites flanking the selectable or screenable marker gene.

16. The method of claim 1, wherein said two flanking DNA regions are about 50 to about 2000 nucleotides in length.

17. The method of claim 8, wherein the sequences common between said first and second repeat sequences are 16 nucleotides in length.

18. The method of claim 8, wherein said DNA sequence of interest comprises between said first and second repeat sequence, two recognition sites for said second DSBI enzyme, said two recognition sites flanking the selectable or screenable marker gene.

19. The method of claim 8, wherein said two flanking DNA regions are about 50 to about 2000 nucleotides in length.

20. The vector of claim 13, wherein the sequences common between said first and second repeat sequences are 16 nucleotides in length.

21. The vector of claim 13, wherein said DNA sequence of interest comprises between said first and second repeat sequence, two recognition sites for a second DSBI enzyme, said two recognition sites flanking the selectable or screenable marker gene.

22. The vector of claim 13, wherein said two flanking DNA regions are about 50 to about 2000 nucleotides in length.

* * * * *

SEQUENCE LISTING

```
<160> NUMBER OF SEQ ID NOS: 4

<210> SEQ ID NO 1
<211> LENGTH: 732
<212> TYPE: DNA
<213> ORGANISM: Artificial
<220> FEATURE:
<223> OTHER INFORMATION: synthetic I-SceI coding region (UIPAC)
<220> FEATURE:
<221> NAME/KEY: variation
<222> LOCATION: (25)..(27)
<223> OTHER INFORMATION: AGA
<220> FEATURE:
<221> NAME/KEY: variation
<222> LOCATION: (73)..(75)
<223> OTHER INFORMATION: AGC
<220> FEATURE:
<221> NAME/KEY: variation
<222> LOCATION: (97)..(99)
<223> OTHER INFORMATION: AGC
<220> FEATURE:
<221> NAME/KEY: variation
<222> LOCATION: (169)..(171)
<223> OTHER INFORMATION: AGA
<220> FEATURE:
<221> NAME/KEY: variation
<222> LOCATION: (172)..(174)
<223> OTHER INFORMATION: AGC
<220> FEATURE:
<221> NAME/KEY: variation
<222> LOCATION: (175)..(177)
<223> OTHER INFORMATION: AGA
<220> FEATURE:
<221> NAME/KEY: variation
<222> LOCATION: (268)..(270)
<223> OTHER INFORMATION: AGC
<220> FEATURE:
<221> NAME/KEY: variation
<222> LOCATION: (289)..(291)
<223> OTHER INFORMATION: AGA
<220> FEATURE:
<221> NAME/KEY: variation
<222> LOCATION: (436)..(438)
<223> OTHER INFORMATION: AGC
<220> FEATURE:
<221> NAME/KEY: variation
<222> LOCATION: (490)..(492)
<223> OTHER INFORMATION: AGC
<220> FEATURE:
<221> NAME/KEY: variation
<222> LOCATION: (502)..(504)
<223> OTHER INFORMATION: AGC
<220> FEATURE:
<221> NAME/KEY: variation
<222> LOCATION: (523)..(525)
<223> OTHER INFORMATION: AGC
<220> FEATURE:
<221> NAME/KEY: variation
<222> LOCATION: (565)..(567)
<223> OTHER INFORMATION: AGA
<220> FEATURE:
<221> NAME/KEY: variation
<222> LOCATION: (631)..(633)
<223> OTHER INFORMATION: AGC
```

```
<220> FEATURE:
<221> NAME/KEY: variation
<222> LOCATION: (637)..(639)
<223> OTHER INFORMATION: AGC
<220> FEATURE:
<221> NAME/KEY: variation
<222> LOCATION: (712)..(714)
<223> OTHER INFORMATION: AGC
<220> FEATURE:
<221> NAME/KEY: variation
<222> LOCATION: (715)..(717)
<223> OTHER INFORMATION: AGC

<400> SEQUENCE: 1
atggcyaarc chcchaaraa raarcgsaaa gtsaacatya araaraacca ggtsatgaac     60
ctsggmccha actcmaarct sctsaargag tacaartcmc arctsatyga rctsaacaty    120
garcarttcg argcyggmat cggmctsaty ctsggmgayg cytacatycg stcmcgsgay    180
garggmaara cytactgyat gcagttcgar tggaaraaca argcytacat ggaycaygts    240
tgyctsctst acgaycartg ggtsctstcm cchcchcaya araargarcg sgtsaaccay    300
ctsggmaacc tsgtsatyac ytggggmgcy caracyttca arcaycargc yttcaacaar    360
ctsgcsaacc tsttcatyct saacaacaar aaracyatyc chaacaacct sgtsgaraac    420
tacctsacyc cyatgtcmct sgcytactgg ttcatggayg ayggmggmaa rtgggaytac    480
aacaaraact cmacyaacaa rtcmatygts ctsaacacyc artcmttcac yttcgargar    540
gtsgartacc tsgtsaargg mctscgsaac aarttccarc tsaactgyta cgtsaagaty    600
aacaaraaca arccyatyat ctacatygay tcmatgtcmt acctsatytt ctacaaccts    660
atyaarccht acctsatycc hcaratgatg tacaarctsc chaacacyat ytcmtcmgar    720
acyttcctsa ar                                                        732

<210> SEQ ID NO 2
<211> LENGTH: 732
<212> TYPE: DNA
<213> ORGANISM: Artificial
<220> FEATURE:
<223> OTHER INFORMATION: synthetic I-SceI coding region

<400> SEQUENCE: 2
atggccaagc ctcccaagaa gaagcgcaaa gtgaacatca agaagaacca ggtgatgaac     60
ctgggaccta acagcaagct cctgaaggag tacaagagcc agctgatcga actgaacatc    120
gagcagttcg aagctggcat cggcctgatc ctgggcgatg cctacatcag atcccgggac    180
gaaggcaaga cctactgcat gcagttcgag tggaagaaca aggcctacat ggaccacgtg    240
tgtctgctgt acgaccagtg ggtcctgagc cctcctcaca agaaggagcg cgtgaaccat    300
ctgggcaacc tcgtgatcac ctggggagcc cagaccttca agcaccaggc cttcaacaag    360
ctggccaacc tgttcatcgt gaacaacaag aagaccatcc ccaacaacct cgtggagaac    420
tacctcactc ccatgagcct ggcctactgg ttcatggacg acggaggcaa gtgggactac    480
aacaagaaca gcaccaacaa gtcaattgtg ctgaacaccc aaagcttcac cttcgaagaa    540
gtggagtacc tcgtcaaggg cctgcgcaac aagttccagc tgaactgcta cgtgaagatc    600
aacaagaaca agcctatcat ctacatcgac agcatgagct acctgatctt ctacaacctg    660
atcaagccat acctgatccc tcagatgatg tacaagctgc ccaacaccat cagcagcgag    720
accttcctga ag                                                        732
```

```
<210> SEQ ID NO 3
<211> LENGTH: 18
<212> TYPE: DNA
<213> ORGANISM: Artificial
<220> FEATURE:
<223> OTHER INFORMATION: recognition site of I-SceI

<400> SEQUENCE: 3
tagggataac agggtaat                                                   18

<210> SEQ ID NO 4
<211> LENGTH: 29
<212> TYPE: DNA
<213> ORGANISM: Artificial
<220> FEATURE:
<223> OTHER INFORMATION: Recognition site of I-CeuI

<400> SEQUENCE: 4
cgtaactata acggtcctaa ggtagcgaa                                       29
```